United States Patent [19]

Moss

[11] Patent Number: 4,688,581
[45] Date of Patent: Aug. 25, 1987

[54] METHOD AND APPARATUS FOR IN VIVO DETERMINATION OF MUSCLE FIBER

[76] Inventor: Crayton L. Moss, 1628 Juniper, Apt. 93, Bowling Green, Ohio 43402

[21] Appl. No.: 913,308

[22] Filed: Sep. 30, 1986

Related U.S. Application Data

[63] Continuation-in-part of Ser. No. 832,325, Feb. 24, 1986.

[51] Int. Cl.$^4$ ............................................... A61B 5/05
[52] U.S. Cl. ................................. 128/741; 128/774; 128/782
[58] Field of Search ...................... 128/741, 774, 782

[56]  References Cited
U.S. PATENT DOCUMENTS

| 4,166,452 | 9/1979 | Generalas | 128/741 |
| 4,236,528 | 12/1980 | Stanec et al. | 128/741 |
| 4,291,705 | 9/1981 | Severnghaus et al. | 128/741 |
| 4,387,723 | 6/1983 | Atlee et al. | 128/741 |
| 4,503,863 | 3/1985 | Katims | 128/741 |

OTHER PUBLICATIONS

Leifer et al, Biomedizinische Technik, vol. 21, (Supplement), Jun. 1976, pp. 113–114.
Kronenwetter et al, Automedica, vol. 1, No. 4, Dec. 1975, pp. 267–271.
Ackmann et al, J. of Clin. Engr., vol 4, No. 4, Oct.-Dec. 1979, pp. 329–337.

Primary Examiner—Kyle L. Howell
Assistant Examiner—John C. Hanley
Attorney, Agent, or Firm—Paul F. Horton

[57] ABSTRACT

A method for non-invasive in vivo determination of muscle fiber composition and apparatus for accomplishing the same. The method includes the steps of electrically stimulating a chosen muscle; determining the stimulation current; measuring the electrical potential of the muscle; the contraction time; and the force produced by the contraction; and by intercorrelating the data by multiple regression, determining the type, percentage and size of muscle fibers within the muscle stimulated. Apparatus for determining the muscle composition includes a muscle stimulator of controlled voltage; electromyogram equipment; and a force transducer providing a tension curve as well as force measurements.

13 Claims, 9 Drawing Figures

MULTIPLE REGRESSION FOR THE FOUR PHYSIOLOGICAL CATAGORIES: (1) ISOMETRIC TENSION, (2) CONTRACTION TIME, (3) ELECTROMYOGRAM, AND (4) CURRENT RECORDED AT THE FOURTH FIVE PERCENT INCREASE OF TENSION.

| PROTOCOL | TYPE II PERCENT | | | | | TYPE II PERCENT (MICRONS) | | | | | TYPE I PERCENT (MICRONS) | | | | |
|---|---|---|---|---|---|---|---|---|---|---|---|---|---|---|---|
| | R | $R^2$ | SEE | df | F | R | $R^2$ | SEE | df | F | R | $R^2$ | SEE | df | F |
| A | 0.74 | 0.55 | 16.0 | 4/16 | 4.81* | 0.71 | 0.50 | 16.7 | 4/16 | 4.05** | 0.83 | 0.69 | 9.7 | 4/16 | 8.97* |
| B | 0.95 | 0.90 | 8.8 | 8/12 | 12.81* | 0.88 | 0.77 | 13.0 | 8/12 | 5.11* | 0.92 | 0.85 | 7.9 | 8/12 | 8.33* |

\* SIGNIFICANT DIFFERENCE ($P < 0.01$)
\** SIGNIFICANT DIFFERENCE ($P < 0.05$)

METHOD AND APPARATUS FOR IN VIVO DETERMINATION OF MUSCLE FIBER

BACKGROUND OF THE INVENTION

1. Field of the Invention

This invention relates, in general, to methods and apparatus for determining the composition of skeletal muscle, and more particularly to a method and apparatus for non-invasive in vivo determination of skeletal muscle composition.

2. Description of the Prior Art

Skeletal muscle fiber is commonly classified into two types--Type I and Type II. Type I muscle has a slow contraction time and a low tension output as compared with type II. A high percentage of Type II muscle fiber is therefore a prerequisite for performing fast contractions with high tension outputs. Determination of muscle fiber composition is important for medical as well as physical education reasons in promoting the understanding of muscle building; atrophy; fatigue; soreness; rehabilitation; effect of exercise; athletic potential; effect of diets; and many other factors.

Prior to the present invention, muscle biopsies with histochemical staining has been used to determine fiber composition of various muscles. In the histochemical technique, thin transverse sections of muscle are caused to adhere to glass cover slips. By incubating and rinsing the sections in solutions of specific chemical composition, the fiber cross sections may be preferentially stained according to their type and metabolic characteristics. The staining intensities from histochemcial procedures are assessed qualitatively, using a light microscope. This process, although appearing simple, requires specific equipment; analyzation is very tedious and time-consuming, and requires a technician specialized in histochemical staining procedure. It is, therefore, apparent that assessment of fiber type through histochemical staining is confined to a specialized facility or laboratory. Further, such histochemical determination obviously results in damage to the muscle being studied, because of the biopsy or biopsies. Such damage, with the obvious discomfiture involved, precludes periodic testing and the subject is often loathe to submit to the biopsies. The method is therefore completely unsuitable for frequent use except for serious medical evaluations.

Relevant work in the area of indirect measurement of physiological profile testing and determination include the studies of Thorstensson, Journal of Applied Physiology 40:12-16, 1976, who has showed a correlation between muscle performance and fast-twitch muscle fibers; Gregor, Journal of Applied Physiology 47:388-392, 1979, who found a correlation between fast-twitch area and torque produced; Lower and Castill, Human Performance Laboratory, Ball State University, 1980; and Petrofsky, Medicial and Biological Engineering and Computing, 17:525-533, 1979, and Petrofsky and Lind, American Journal of Physiology 36:185-196, 1979, showing muscle response to stimulation voltage.

SUMMARY OF THE INVENTION

The present invention, for the first time, shows a method for in vivo, non-invasive determination of muscle fiber composition as to type, percentage distribution, and size, and apparatus for accomplishing the same.

The method of the present invention includes the steps of measuring current necessary to stimulate a given muscle; measuring the contraction of the muscle, both as to force and time; measuring electrical potentials of the muscle before and during contraction; and intercorrelating such data to determine muscle composition. The apparatus of the present invention is used to obtain the necessary data. A more complete description of the invention may be found in the appended claims. It is therefore a primary object of the present invention to provide a method of in vivo determination of muscle fiber composition.

More specifically, it is an object of the present invention to provide a method of non-invasive in vivo determination of muscle fiber composition.

It is also a fundamental object of the present invention to provide apparatus for the non-invasive in vivo determination of muscle fiber composition.

Additional objects and advantages will become apparent and a more thorough and comprehensive understanding may be had from the following description taken in conjunction with the accompanying drawings forming a part of this specification.

DETAILED DESCRIPTION OF THE INVENTION

Figure 1:
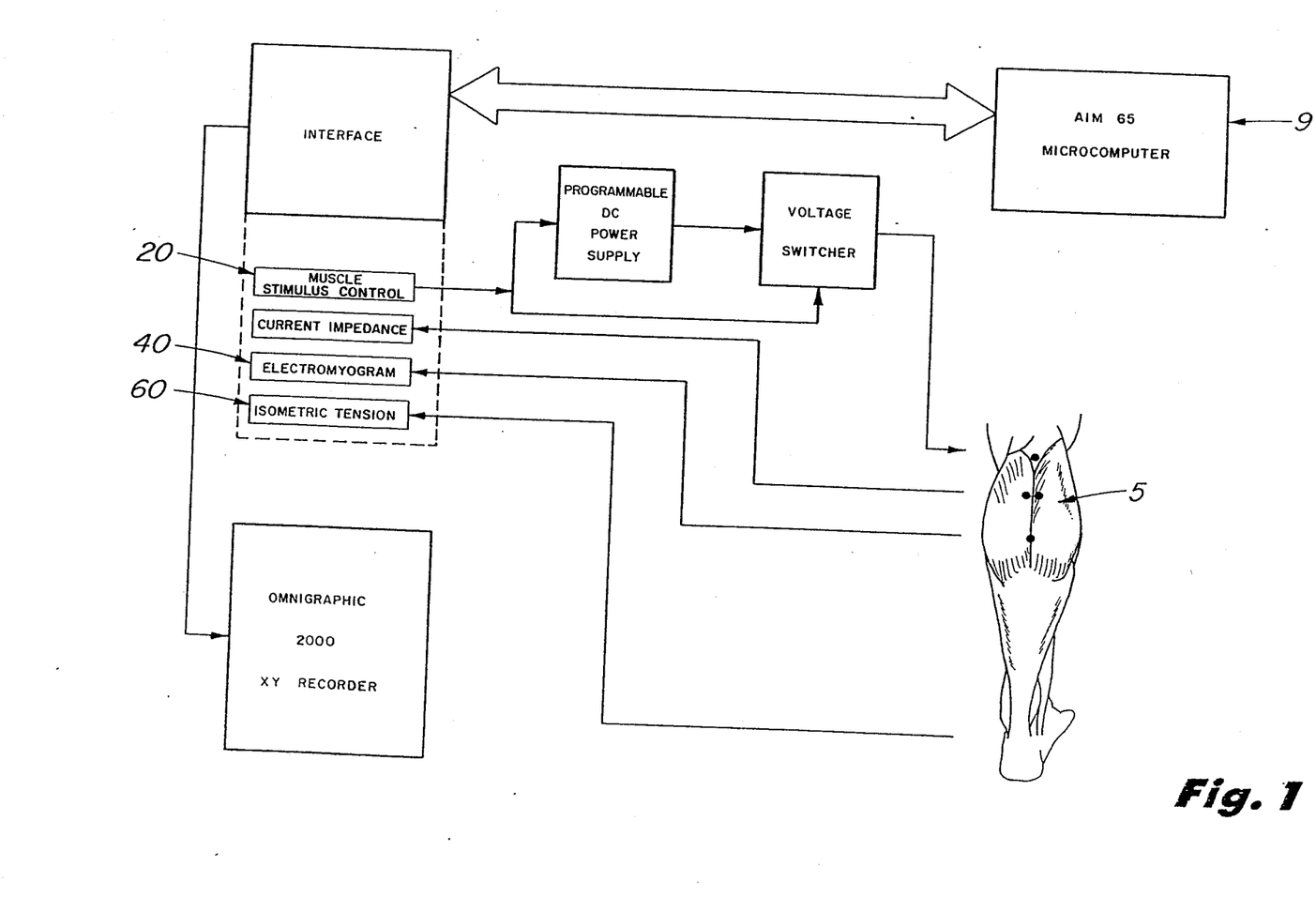
FIG. 1 is a schematic showing the general system used in the method of the present invention.

Referring now to FIG. 1, a schematic showing some of the apparatus and its relationship to the determination of muscle composition in one selected muscle, the gastrocnemius muscle 5 of the leg, may be seen. The apparatus includes, generally, means for electrical stimulation of the muscle, designated by the numeral 20; means 40 for measuring electrical potentials of the muscle; and means for measuring contraction time and force of contraction of a muscle, designated generally by the numeral 60.

Electrical stimulation means 20 receives electricity from any conventional power source. The stimulation means includes a conventional power supply, preferably direct current and providing a pulse duration set at .4 milliseconds for comfort. Means 20 also includes two or more surface electrodes which may be constructed of carbon-rubber for chronic transcutaneous electrical muscle stimulation. The electrodes are preferably attached to the skin using an electrode tape patch.

Before electrodes are attached, motor points of the muscle are first located. There are two main motor points for both the lateral and medial head of the gastrocnemius. With the stimulator current off, one positive electrode is temporarily secured to the limb and the negative electrode is placed over the appropriate muscle—in the example provided, the gastrocnemius. The pulse repetition frequency is set at a low level to minimize muscle fatigue during the search. When the stimulator is triggered to "on", the current amplitude is slowly increased until a small, barely perceptible motor response is elicited. Without modifying the amplitude, the negative electrode is moved over the muscle area between periods of stimulation until the greatest motor response is observed. This area is then marked, as by a colored marker. To localize the motor point to a pin point size area, a neural point finder, conventional in the art, is used.

The negative electrode of the stimulator is then positioned on the two center motor points, while the positive electrode is positioned approximately 20 mm. above the negative electrode on the upper portion of the muscle. Prior to positioning the electrodes, the skin is cleaned with alcohol and abraded with conventional paste. Each electrode is then coated with conductive gel to facilitate the electric current with each pulse duration.

Next, impedance between the two electrodes and including the electrodes and their interface gel is computed and calculated by use of the computer 9. This is accomplished and converted by having the computer analyze the leg's impedance with a known resistor and converting the known different into milliamps of current.

Means 40 for measuring the electrical potential of the muscles is conventional in the art and known as electromyogram equipment. The electromyogram is used to pick up millivolt differences between a resting muscle potential and an active-contracting muscle potential. The surface electromyogram is recorded from the active muscle by one unipolar monitoring electrode, located approximately 70 mm from the distal end of the negative stimulator electrode. The "difference" regulated (negative) electrode may be located on the subject's right hand, centered both lateral and medial between the wrist and knuckle on the posterior aspect of the hand. Prior to positioning the electrodes, the skin and electrodes receive the same standardization as above described for the stimulator electrodes. The electrical potentials of the muscles are measured prior to and during contraction and the the millivolt potentials obtained are stored into the memory of the computer.

Figure 2:
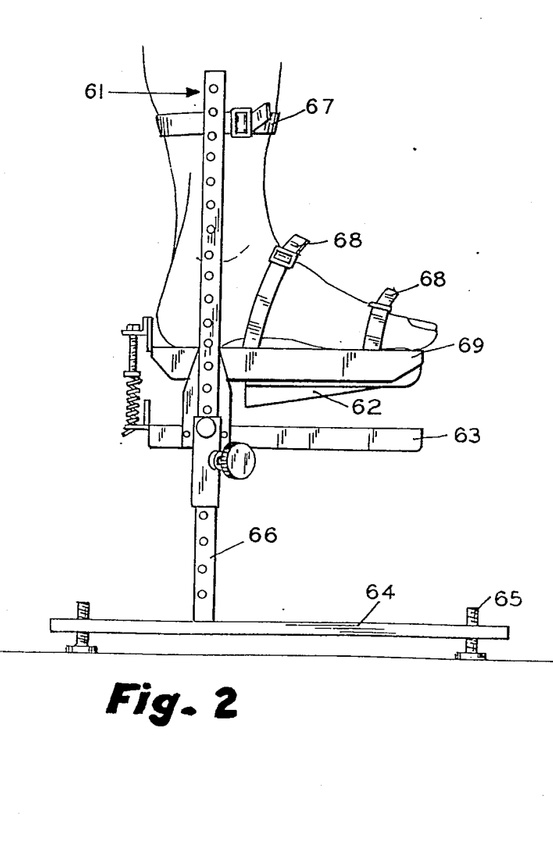
FIG. 2 is a side elevation of the force measuring means of the present invention as may be used on the leg and foot.
Figure 3:
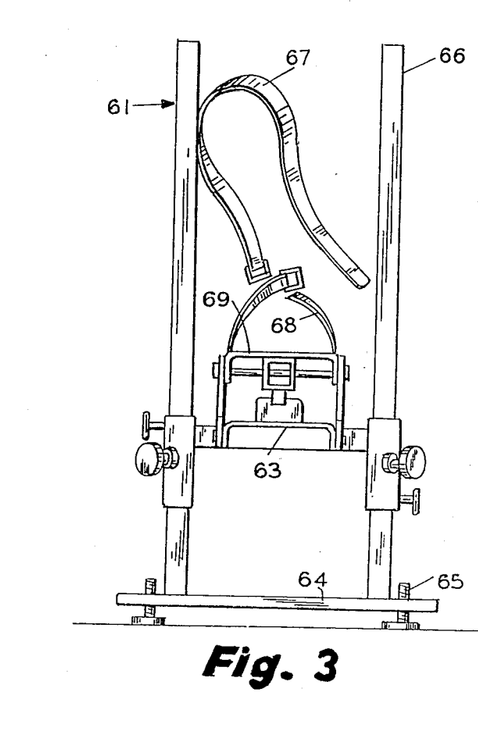
FIG. 3 is a front elevation of the apparatus of FIG. 2.

Means 60 for measuring contraction time and force of contraction is shown to advantage in FIGS. 2 and 3. Means 60 includes a body restraining member, designated by the numeral 61, a platform 63, and a force transducer 62. Body restraining member 61 serves to immovably secure the body part in which one end of the selected muscle terminates. In the present example, restraining member 61 is in the form of a standard 66 supported by a base plate 64 which may be leveled by leveling screws 65. Standard 66 has one or more straps 67 affixed thereto for strapping the calf of the leg to the standard. Platform 63 is temporarily but immovably secured to the standard, extending outwardly transverse thereto. Overlying the platform, a pivotal appendage plate 69, having one or more straps 68 for securing the appendage, may be provided. In the apparatus shown, the appendage plate is in the form of a foot plate with foot strap. Between the appendage or the appendage plate and platform 63 is located the force transducer 62. Transducer 62 produces an electrical output under pressure of the foot for the duration of the contraction and at levels depending upon the force of the contraction. The latency period, ie., the period from the time of stimulus to the time of contraction, can thereby be measured as well as the time period from stimulus to peak or maximum contraction. Also measurable by the transducer is the length of time required for muscle to relax from peak tension to one-half that value.

Computer 90 is preferred for intercorrelating the electrical data obtained from the measuring devices, ie. the muscle stimulator, electromyogram, and the transducer. The high speed computer has made it possible to analyze large quantities of complex data with relative ease. Multiple regression has been one of the most important branches of multivariate analysis and the use of multiple regression is well known in the analysis of variance. It is a general statistical technique through which one can analyze the relationship between dependent variables, in the present instance, the percentage of fast twitch, type II, motor fibers, the size of fast twitch fibers and the size of slow twitch, Type I, fibers, and a set of independent or predictor variables, in the present instance tension values, contraction times, current, and EMG.

Figure 4:
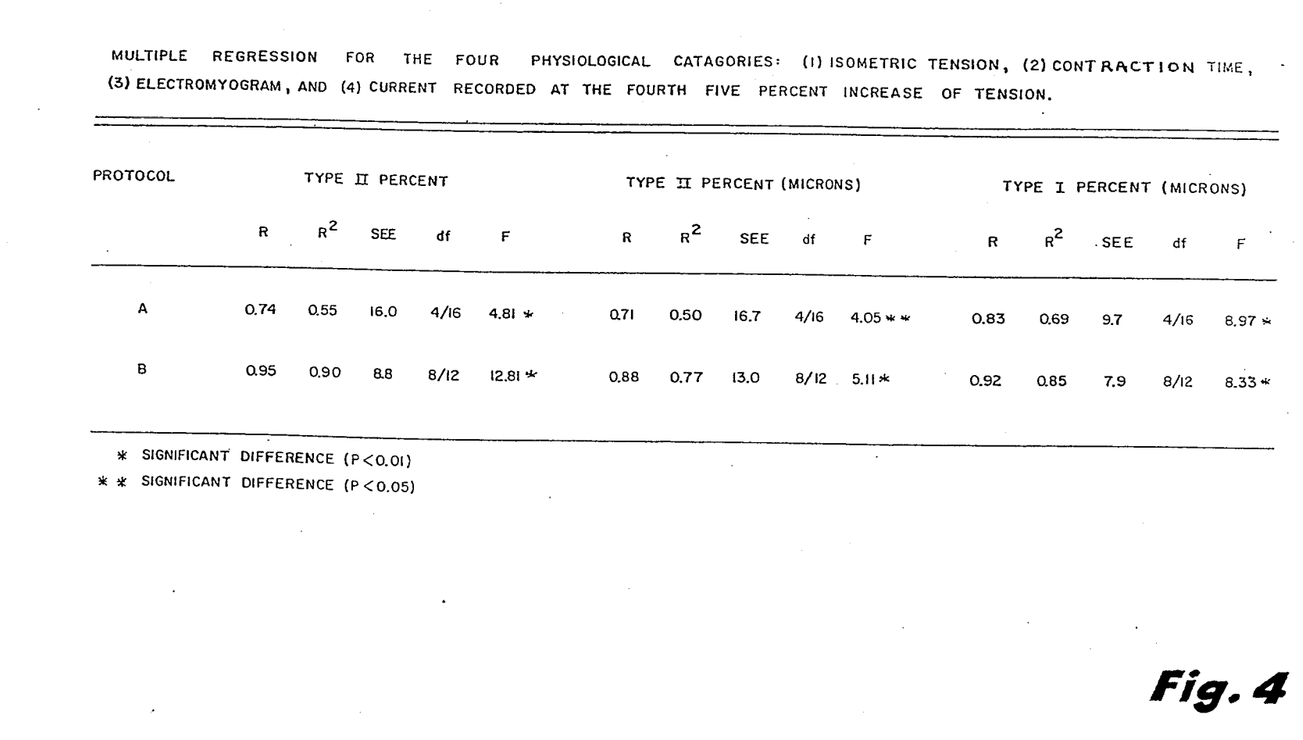
FIG. 4 is a table showing multiple regression of the four physiological categories, as determined in one experiment, used in the determination of muscle fiber composition.

Referring now to FIG. 4, a table showing multiple regression for the four physiological categories, namely isometric tension, contraction time, electromyogram, and current recorded, may be seen. Two protocols were used in experiment in the determination of Type II percent; Type II percent area; and for Type I percent and type I area. The first protocol "A" used the above factors. The second protocol "B" utilized a breakdown in tension into latency, peak, and one-half peak contraction times. Given in the table are multiple correlation (R), multiple correlation square (R*R), standard error of estimate (SEE), and F values. Protocol "A" had lower multiple correlations when compared to protocol "B", but both showed significant F values when related to histochemical analysis.

For determination of the muscle fiber composition of the gastrocnemius, the subject was first asked to lie down on his stomach on an athletic training examination table and shown how motor points are located and what an EMS (electrical muscle stimulation) pulse felt like. Motor points were then located and the skin prepared. Impedance between electrodes were then recorded. The subject was then seated, one leg, ie. ankle, being strapped into position by straps 67, shown in FIGS. 2 and 3. The subject was instructed to lean back and relax with arms to the side. The foot under study was then strapped to movable foot plate 69. Each instrument interconnection was arranged according to FIG. 1 and the subject's electrodes were then connected. Once the subject was relaxed, power supplies and instruments were activated. Stimulation impulses began and ended according to a flow diagram, now shown, of the computer to measure contractile characteristics of the muscle fibers.

For each subject in the study, a 55 volt DC electrical muscle stimulus was used. Because of different body impedances for each subject, and because current is the means by which muscles are stimulated, conversion factors are required to determine current as well as contraction times. Obviously, differing voltage stimulation would require differing conversion factors. Conversion formulae for 55 volts stimulation are as follows:

64 mA/recorded mA=(ImA)
444 ms/sum of contraction times in ms=(Tms)
247 ms/sum of type II contraction times in ms=(IIms)
242 ms/sum of type I contraction times in ms=(Ims).
mA=milliampere; ms=milliseconds.

All conversion factors are averages obtained from and based on twenty one subjects studied.

Sum of type II=Type II contraction time+Type II? contraction time+type II ½ relaxation time+latency time. Sum of type I=Type I contraction time+Type II? contraction time+type I ½ relaxation time+latency time.

To determine the number of motor units which were contracted by a given stimulus, the following formula was used, ie. EMG mV/130 mV=(mu). mV=millivolts. Motor units are the fundamental units of neuromuscular contraction. A motor unit is the group of muscle fibers innervated by a single nerve fiber. A normal motor unit has a characteristic action potential giving a spike which lasts 0.5 seconds and obtains an amplitude of approximately 130 mV, as is well known in the art. Since 130 mV equals the EMG output of one motor unit, the number of motor units is found by dividing the EMG by 130.

Other formula used in the calculations are as follows:
Sum of Tensions (TKg)=type II tension+type II? tension+Type I tension.
Sum of Type II Tensions (IIKg)=Type II tension+type II? tension.
Sum of Type I Tensions (IKg)=Type I tensions.

Figure 5:
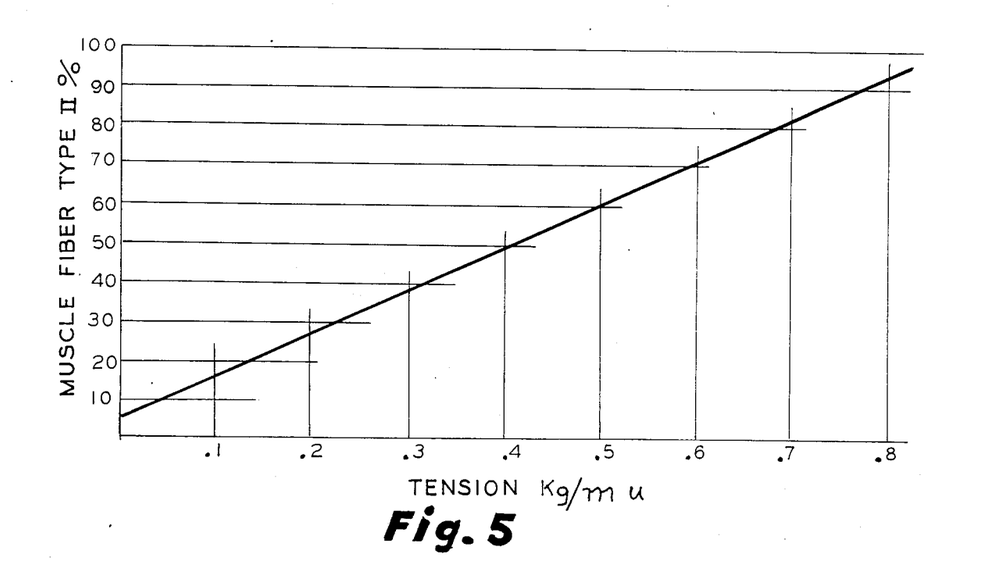
FIG. 5 is a graph showing the relationship between Tension Kg/mu and percent of Type II muscle fiber.

Formula for determining muscle fiber type II percent is ((TKg) (ImA) (Tms))/(mu)=Tension Kg/mu. Percentage may be obtained by referring to the graph, FIG. 5. R=0.95.

Figure 6:
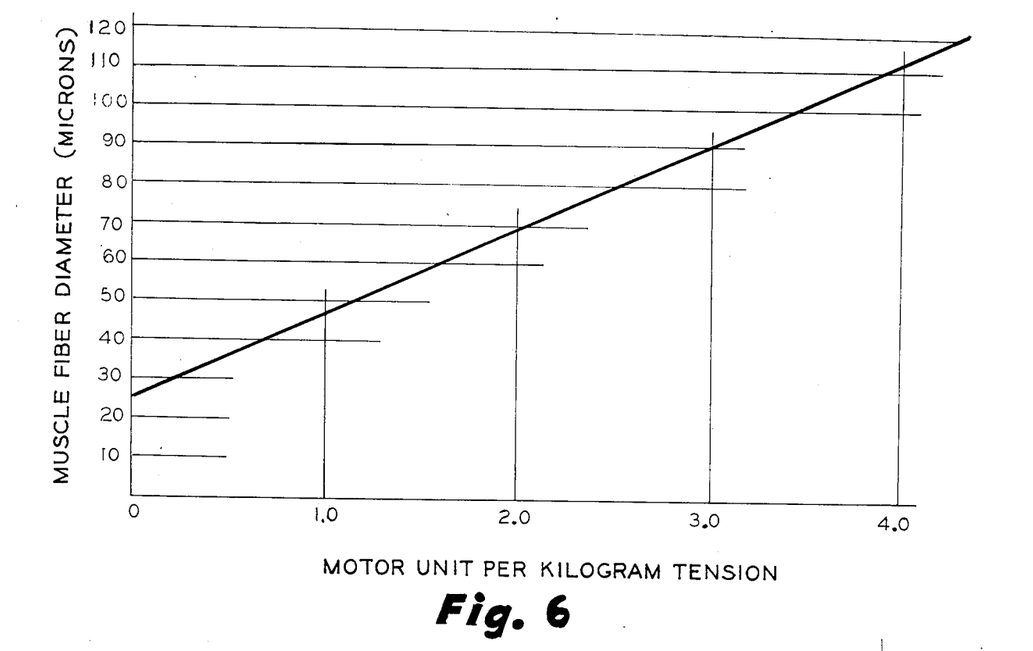
FIG. 6 is a graph showing the relationship between muscle fiber diameter and Tension expressed in Motor Units per kilogram for Type II fiber.

Formula for determining type II muscle fiber diameter; R=0.88 is (mu)(type II%)/((IIKg) (ImA) (IIms))-=number of motor units per kilogram. Diameter may be obtained by referring to the graph, FIG. 6.

Figure 7:
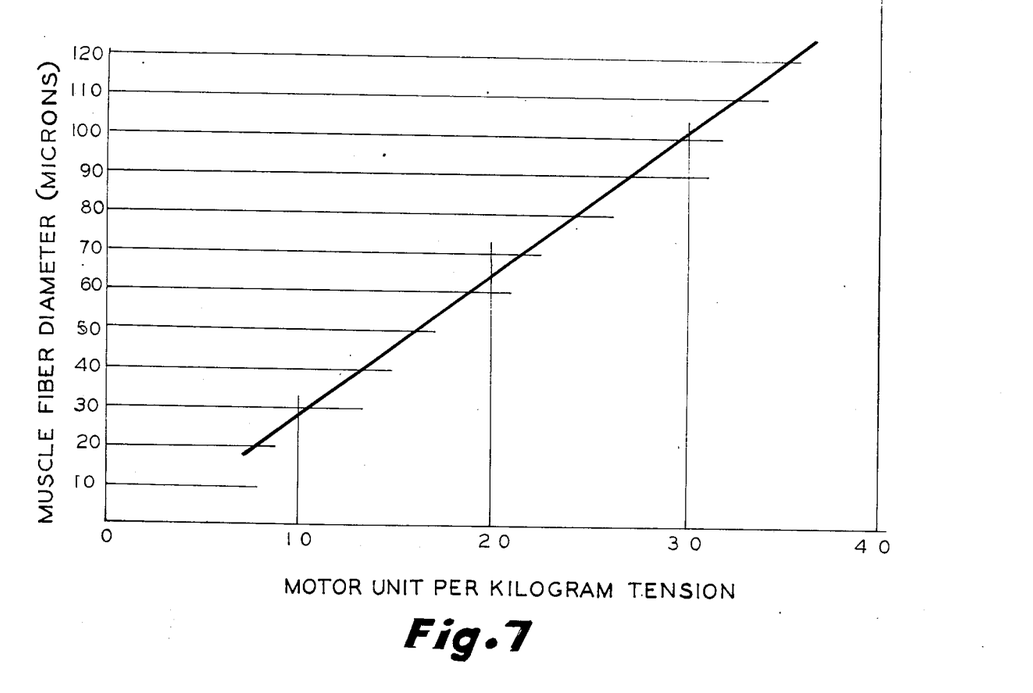
FIG. 7 is a graph showing the relationship between muscle fiber diameter and Tension expressed in Motor Unit per kilogram for Type I fiber.

Formula for determining fiber type I diameter, R=0.92 is (mu) (Type II%)/((Ikg) (ImA) (Ims))=number of motor units per kilogram. Diameter may be obtained by referring to the graph, FIG. 7.

While formulae are given for an example to follow and to make clear the intercorrelation on a given set of data, it is assumed that all formulae will be programmed into computer 9 and data will be fed directly into the computer as indicated.

Figure 8:
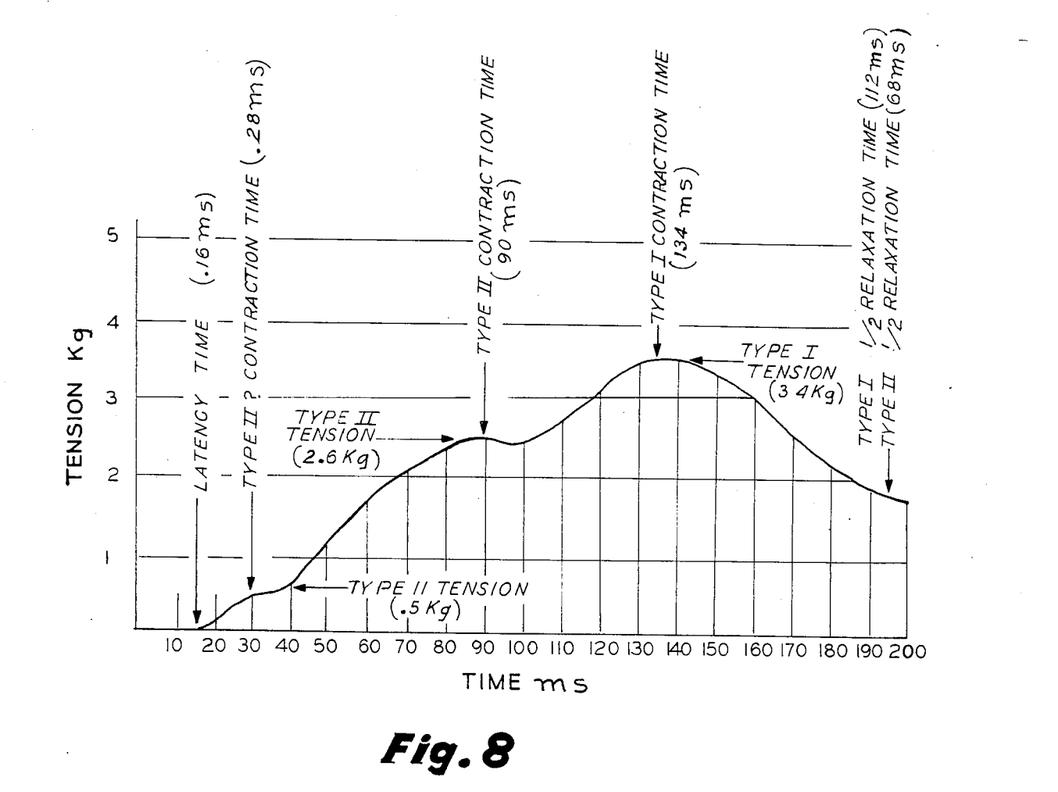
FIG. 8 is a model of a muscle contraction curve plotting contraction vs. time and indicating specific criteria of the curve used for calculations.

Tension and contraction time are determined by a curve plotting tension versus time; a model of which is shown in FIG. 8. Terms used and parameters are given below:
a. Latency. Time from stimulus to beginning of contraction. 16 ms (+ −8).
b. Type II?. Unknown muscle fiber. Fast twitch. Time from stimulus to where tension is the highest in time range. Highest peak in time frame is both tension and contraction time for type II?. 28 ms (+ −10) time range.
c. Type II. Fast twitch. Time from stimulus to where tension is the highest in time range. Highest peak in time frame is both tension and contraction time for type II. 90 ms (+ −30) time range.
d. Type I. Slow Twitch. Time from stimulus to where tension is the higheset in time range. Highest peak in time frame is both tension and contraction time for type I. 134 ms (+ −30) time range.
e. Type II—½ Relaxation. Time from stimulus to where tension is ½ of type II tension. This time minus type II contraction time=Type II ½ Relaxation time.
f. Type I—½ Relaxation. Time from stimulus to where tension is ½ of Type I tension. This time minus type I contraction time=type I ½ Relaxation time.

Utilizing the above definitions and formulae, the following example will show how muscle fiber type percentage and diameter are determined.

EXAMPLE

Figure 9:
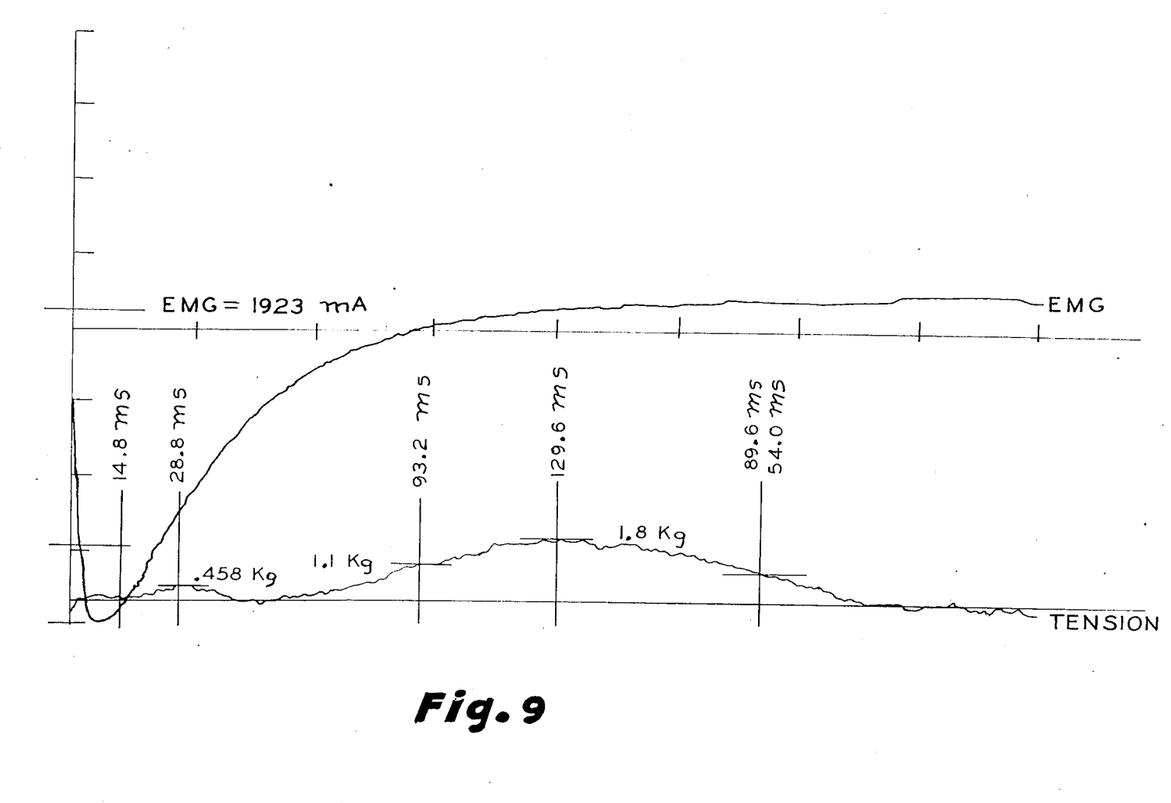
FIG. 9 is a sketch of an actual recording showing tension curve and EMG curve of one subject for determination of muscle fiber composition.

Referring now to FIG. 9, an actual recording of one test on one subject may be seen. The upper curve represents the EMG curve; the lower curve the contraction time and tension curve. The following information was recorded:
1. 55 volt stimulus.
2. 67.3 mA current.
3. 1923 mV EMG.
4. Contraction time & tensions:
   a. Latency. 14.8 ms.
   b. Type II? contraction time. 28.8 ms. Type II? tension. 0.458 kg.
   c. Type II contraction time. 93.2 ms. Type II tension. 1.10 kg.
   d. Type I contraction time. 129.6 ms. Type I tension. 1.83 kg.
   e. Type II ½ relaxation time. 89.6 ms.
   f. Type I ½ relaxation time. 54.0 ms.

Using the conversion factors, the following data is produced:
1. 1923 mV/130 mV=14.79 (mu)
2. 64 mA/67.3 mA=0.951 (ImA)
3. 444 ms/407 ms=1.091 (Tms)
4. 247 ms/226 ms=1.093 (IIms)
5. 242 ms/224 ms=1.08 (Ims)
6. (TKg)=3.39 Kg.
7. (IIKg)=1.56 Kg.
8. (IKg)=1.83 Kg.
9. (3.39 Kg)(0.951)(1.091)/14.79 mu=0.237 Kg/mu. Referring to the graph, FIG. 5, it will be seen that 0.237 Kg/mu=31% Type II muscle fiber. The muscle biopsy on the same subject shows 30% Type II muscle fiber.
10. (14.79)(0.31)/((1.56 Kg)(0.951)(1.092))=2.83 mu/Kg. Referring to the graph, FIG. 6, it will be seen that 2.83 mu/Kg=84 u (micron) diameter for Type II muscle fiber. The muscle biopsy showed a 90 micron diameter.
11. (14.79)(0.31)/((1.83 Kg)(0.951)(1.08))=1.95 mu/Kg. Referring to the graph, FIG. 7, it will be seen that 1.95 mu/Kg=72 micron diameter for type I muscle fiber. The muscle biopsy showed 70 micron diameter.

Having thus described in detail a preferred selection of embodiments of the present invention, it is to be appreciated and will be apparent to those skilled in the art that many physical changes could be made in the apparatus and other changes could be made in the method of the present invention without altering the inventive concepts and principles embodied therein. The present embodiments are therefore to be considered in all respects as illustrative and not restrictive, the scope of the invention being indicated by the appended claims rather than by the foregoing description, and all changes which come within the meaning and range of equivalency of the claims are therefore to be embraced therein.

I claim:

1. Apparatus for non-invasive determination of the composition of skeletal muscle fiber comprising:
   means for electrically stimulating a selected muscle to contraction at a controlled and measured voltage;
   means for measuring electrical potentials of the muscle;
   means for measuring contraction time of the muscle; and means for measuring force produced by the contraction of said muscle during stimulation; and
   intercorrelator means for intercorrelating the measurement for determining muscle fiber composition.

2. The apparatus as described in claim 1 wherein said means for measuring force produced by contraction of said muscle includes:
   a body restraining member for immovably securing the body part in which one end of said selected muscle terminates; and
   a force transducer for measuring force exerted by an appendage to which the other end of said selected muscle terminates.

3. The apparatus as described in claim 1 wherein said means for measuring force produced by contraction of said muscle includes:
   a body restraining member for immovably securing the body part in which one end of said selected muscle terminates;
   a platform affixed to said restraining member; and
   a force transducer in contact with said platform and with an appendage to which the other end of said muscle terminates to determine force between said appendage and said platform.

4. The apparatus as described in claim 3 wherein said body restraining member is provided with an upright standard and at least one strap engageable with the standard and the body part to restrain the body part to said standard; wherein said platform is immovably secured to said standard; and wherein said transducer is disposed between said platform and the appendage in which the muscle terminates.

5. A method for in vivo determination of muscle fiber composition comprising the steps of:
   measuring current necessary to stimulate a selected muscle to a desired contraction;
   measuring electrical potentials of said muscle prior to and during contraction caused by said stimulation;
   measuring the contraction time of the muscle;
   measuring force produced by the contraction of the muscle; and
   intercorrelating said stimulating current, said electrical potentials; said contraction times; and said force to determine the fiber composition of the muscle.

6. The method as described in claim 5 wherein the step of measuring current necessary to stimulate a selected muscle to contraction includes the steps of:
   determining the motor point locations for the muscle;
   placing stimulator electrodes at selected motor points;
   measuring impedance between said electrodes;
   stimulating said muscle by said electrodes at selected voltages; and
   determining the current values for said stimulation.

7. The method as described in claim 5 wherein the step of measuring electrical potentials of said muscle includes the steps of:
   placing at least two electrodes at selected locations relative to the selected muscle; and
   measuring voltage difference between said electrodes.

8. The method as described in claim 5 wherein the step of measuring the contraction time of the muscle includes the steps of:
   measuring the latency period from time of stimulus to time of muscle contraction rseponse;
   measuring the time period from end of stimulus to peak tension produced by the muscle contraction; and
   measuring the length of time for muscle relaxation from peak tension produced to one-half the peak tension.

9. A method for non-invasive in vivo determination of muscle fiber composition comprising the steps of:
   electrically stimulating a selected muscle, at least one end of which terminates in an appendage, at a selected voltage to a desired contraction;
   measuring the electrical potentials of the muscle before and during contraction;
   measuring the time of said contraction;
   measuring the force produced by said contraction by restraining the body portion containing one end of said muscle and by placing a force transducer in contact with the appendage in which the opposing end of said muscle terminates to determine force exerted during contraction;
   correlating current produced by said stimulation voltage; said muscle potentials; said contraction time; and said force of contraction; and
   determining from said correlation the fiber composition of the muscle stimulated.

10. The method as described in claim 9 wherein the step of electrically stimulating a selected muscle includes the steps of:
    determining the motor point locations for the muscle;
    placing stimulator elecrodes at selected motor points;
    measuring impedance between said electrodes;
    stimulating said muscle at selected voltages; and determining the current values for said stimulation.

11. The method as described in claim 9 wherein the step of measuring electrical potentials of said muscle includes the steps of:
    placing at least two electrodes at selected locations on the skin relative to the selected muscle; and
    measuring voltage difference between said electrodes.

12. The method as described in claim 9 wherein the step of measuring the contraction time of the muscle includes the steps of:
    measuring the latency period from time of stimulus to time of muscle contraction;
    measuring the time period from stimulus to peak tension produced by the muscle contraction; and
    measuring the length of time for muscle relaxation from peak tension to one-half peak tension.

13. The method as described in claim 9 wherein the muscle stimulated is the human gastrocnemius and wherein the step of measuring the force produced by said contraction includes the steps of:
    strapping the ankle to a rigid object;
    strapping the foot to a foot plate;
    placing a force transducer between the foot and plate; and
    determining the force exerted on said transducer during stimulated contraction of the muscle.

* * * * *